United States Patent
Ence et al.

(10) Patent No.: US 6,581,451 B2
(45) Date of Patent: Jun. 24, 2003

(54) DEVICE FOR MEASURING DENSITY OF MATERIAL FLOWING IN A CONVEYING DUCT

(75) Inventors: Brian Ence, Lansdale, PA (US); Maurice James Kelley, Paoli, PA (US)

(73) Assignee: CertainTeed Corporation, Valley Forge, PA (US)

( * ) Notice: Subject to any disclaimer, the term of this patent is extended or adjusted under 35 U.S.C. 154(b) by 106 days.

(21) Appl. No.: 09/952,467

(22) Filed: Sep. 14, 2001

(65) Prior Publication Data

US 2003/0051547 A1 Mar. 20, 2003

(51) Int. Cl.[7] .............................................. G01F 23/00
(52) U.S. Cl. ......................................................... 73/149
(58) Field of Search ................................ 73/149, 32 R, 73/433

(56) References Cited

U.S. PATENT DOCUMENTS

| | | |
|---|---|---|
| 6,047,518 A * | 4/2000 | Lytle ........................ 52/742.13 |
| 6,055,856 A | 5/2000 | Senne |
| 6,082,639 A | 7/2000 | Pentz et al. |
| 6,088,968 A | 7/2000 | Williston, Jr. et al. |

* cited by examiner

Primary Examiner—Richard A. Moller
(74) Attorney, Agent, or Firm—Duane Morris LLP

(57) ABSTRACT

A device for determining density of a material flowing in a conveying system includes a duct segment in fluid communication with the conveying system. The duct segment is coupled to the conveying system by isolation fittings, which allow the weight of the duct segment to be measured independent of the weight of adjacent portions of the conveying system. Further, a method for determining density of a material flowing in a conveying system includes weighing a duct segment having material free fluid flowing therein. The duct segment having a mixture of material and fluid flowing therein is also weighed. The difference of the two weights is used to determine a linear density of the material.

18 Claims, 2 Drawing Sheets

DEVICE FOR MEASURING DENSITY OF MATERIAL FLOWING IN A CONVEYING DUCT

FIELD OF THE INVENTION

The present invention relates to devices and methods for measuring properties of materials in fluids, and particularly to determining the density of materials in pneumatic or hydraulic conveying systems.

BACKGROUND

Due to cost-effectiveness, speed and ease of application, and thoroughness of coverage in both open and confined areas, the practice of using pneumatically delivered (e.g., blown or sprayed) fibrous insulation materials, such as fiberglass, is a popular method for installing insulation in new and existing buildings. Components of a typical blown delivery system include a source of insulation material, conduit means (e.g., ducts) for conveying the insulation material from the source to the installation site, and a source of pressurized air such as a compressor, blower or the like, for generating a flow of pressurized air for entraining the insulation material and delivering it from the source through the conduit means for discharge at the installation site.

Typically, the insulation material used in conventional insulation spraying and blowing machines is packed in bags, or is baled, for shipment to the user. Upon being opened, these bags or bales are emptied into the receiving hopper of a conventional insulation spraying and blowing machine. The insulation material in the hopper is then dispensed by the system.

Of particular interest is monitoring and determining the amount of insulation material dispensed by the system. One previous technique for monitoring and determining the amount of material dispensed by the system includes counting the number of bags or bales that have been emptied into the hopper. A disadvantage of this technique is that the bag or bale size is often not commensurate with the amount of insulation material required. For example, a particular application may require 10.2 bales of insulation material. It is difficult to determine that $2/10$ of a bale has been dispensed by visually inspecting the hopper.

Another technique involves measuring the amount of insulation material delivered at the installation site. This technique is often impracticable because access to the installation site is limited or non-existent. For example, it is not practicable to measure the delivered amount of insulation material inside a wall of a building.

A further disadvantage of the above-described techniques is that the amount of insulation material dispensed is not determined in a manner timely enough to allow controlling the pneumatic conveying system (e.g., turn system off when required amount of material has been delivered). Thus, a need exists for a more accurate technique for monitoring and determining the amount of material being dispensed by the system. Further, a need exists for an in situ, real time, dynamic, system and technique for measuring airborne material in a pneumatic conveying system.

SUMMARY OF THE INVENTION

A device for measuring, in situ, the density of a material flowing in a duct includes a duct segment in fluid communication with a conveying system. The weight of the duct segment is measured independent of the weight of adjacent portions of the conveying system.

Advantages of a device in accordance with the present invention include real time measurement of material flow, weight and delivery amount; accurate measurement of material flow, weight, and delivery amount; and real time control of the delivery system. A further advantage of a device in accordance with the present invention is the ability to monitor material delivery amount in situations which are otherwise impracticable (e.g., measured the amount of delivered amount of insulation material inside a wall).

Further, a method for measuring, in situ, the density of a material flowing in a duct includes weighing a duct segment having material free fluid flowing therein to obtain a first weight. The duct segment having a mixture of material and fluid flowing therein is also weighed to obtain a second weight. The first weight is subtracted from the second weight to determine the weight of the material. The weight of the material is divided by the length of the duct segment to determine, in situ, the linear density of the material in the duct segment.

BRIEF DESCRIPTION OF THE DRAWINGS

The above and other advantages and features of the present invention will be better understood from the following detailed description of the preferred embodiments of the invention, which is provided in connection with the accompanying drawings. The various features of the drawings may not be to scale. Included in the drawing are the following figures.

DETAILED DESCRIPTION

Figure 1:
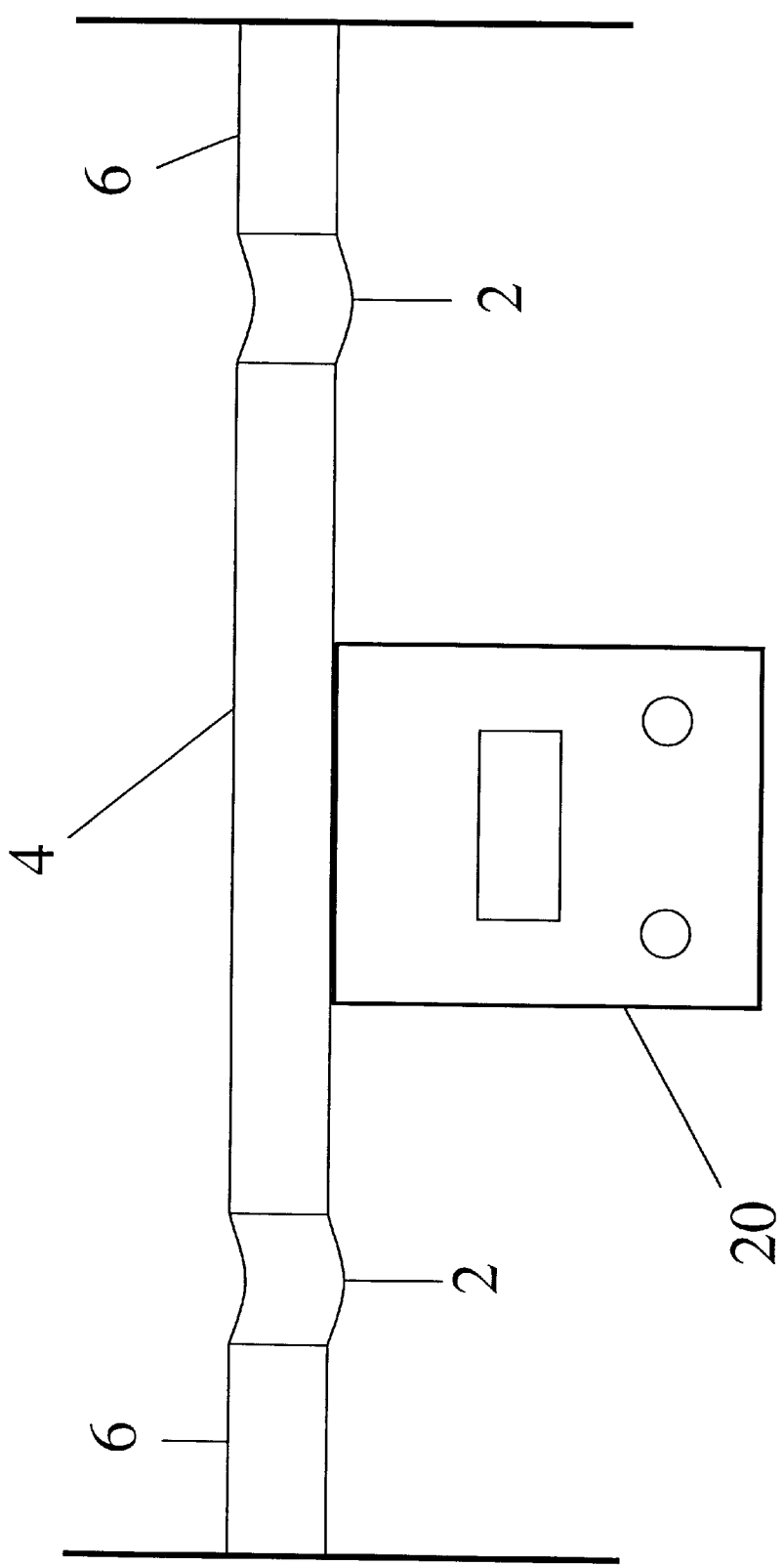
FIG. 1 is a diagram of a system for determining density in accordance with an exemplary embodiment of the invention.

This description is intended to be read in connection with the accompanying drawings, which are to be considered part of the entire written description of this invention. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

FIG. 1 is a diagram of a duct segment 4, isolation fittings 2, support mechanism 20, and adjacent duct portions 6 of a pneumatic conveying system in accordance with an exemplary embodiment of the invention. FIG. 1 shows a conveying system for conveying materials embedded in a fluid. The fluid may be either a gas, a mixture of gases (e.g., air), a liquid, or combination thereof. The types of materials which may be conveyed include generally, but not exclusively, fibers such as granulated rock wool, granulated mineral fiber wool, glass fiber materials, polystyrene, cellulose fibers, expanded mica, asbestos, combinations of these materials, and other types of insulation material. This insulation material may be in particulate form and may be either blown dry or sprayed through a nozzle with liquid added to form an insulating and/or sealing coating. The insulation material used in conventional insulation spraying and blowing machines is typically in a relatively loose condition and packed under high compression in bags or baled for shipment. Upon being opened, these bags or bales are typically manually emptied into the receiving hopper of a conventional insulation spraying and blowing machine to be transferred to the installation site.

The following description is of an embodiment of the invention wherein the material is conveyed by being entrained in air. The invention, however, is not limited to material being entrained in air. Material may be entrained in other substances, such as liquids, other gases, and combinations thereof. The conveying system may be either pneumatic or hydraulic.

Figure 2:
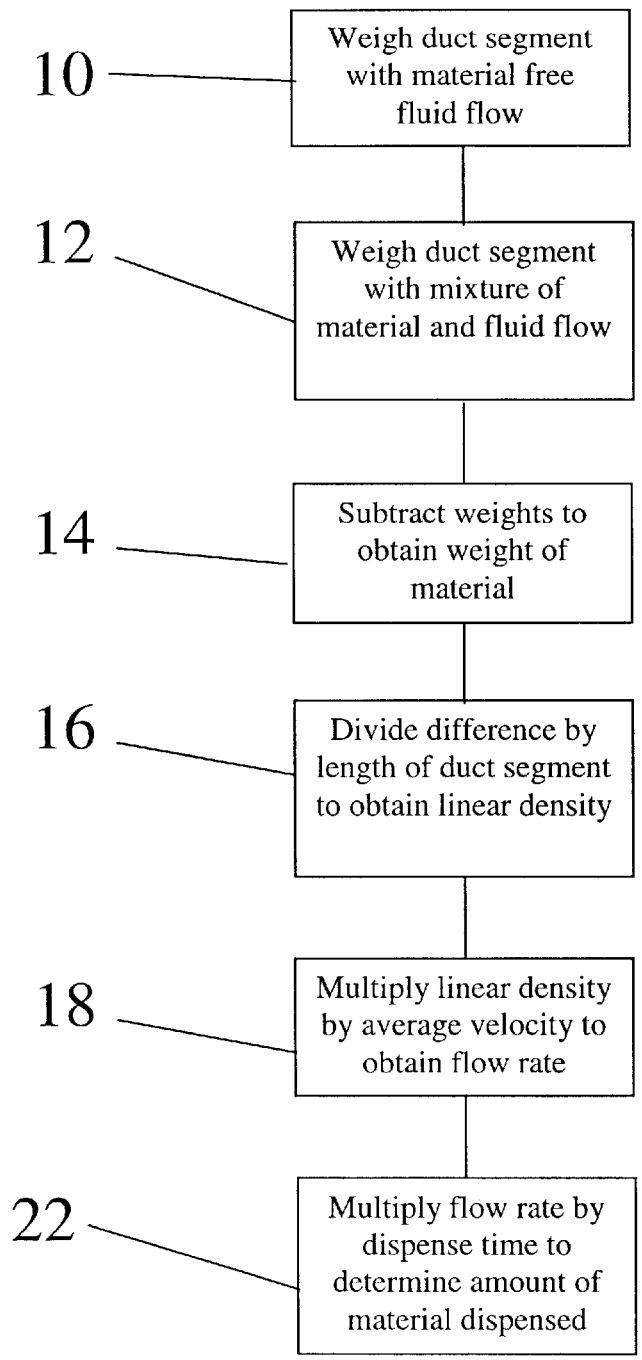
FIG. 2 is a flow diagram of an exemplary embodiment of a process for determining density in accordance with the present invention.

As shown in the preferred embodiment of FIG. 1, material, which is dispersed in an airflow, is transported through the pneumatic conveying system and through duct segment 4. As explained in detail with reference to FIG. 2, the density of the material being transported may be determined by measuring the weight of duct segment 4 with and without material in the airflow. Isolation fittings 2 allow duct segment 4 to be weighed independent of the weight of adjacent duct portions 6.

In an exemplary embodiment of the invention, duct segment 4 and adjacent duct portions 6 are approximately horizontal. Preferably, the duct portions 6 and the duct segment 4 are approximately the same shape, for example rectangular or cylindrical. Further, isolation fittings 2 and adjacent duct portions 6 are approximately straight. Isolation fittings 2 are flexible. The curvature of isolation fitting 2, as shown in FIG. 1, is exaggerated to illustrate the flexibility of isolation fittings 2. The isolation fittings 2 may comprise any lightweight, flexible material and configuration suitable for transporting the conveyed material, for example, plastic, rubber, and/or spiral wound hoses. The isolation fittings 2 may be adhesively attached to the duct segment 4 and the adjacent duct portions 6, or may comprise a flexible sheathing covering the duct segment 4 and the adjacent duct portions 6. The isolation fittings 2 pneumatically couple duct portions 6 to duct segment 4. The adjacent duct portions 6, duct segment 4, and isolation fittings 2 are sufficiently straight and are sufficiently aligned to suppress flow turbulence, and to allow the material being transported to assume a steady, approximately horizontal flow. This steady, approximately horizontal flow allows for accurate weight measurements.

In another exemplary embodiment of the invention, support mechanism 20 is implemented to support the duct segment 4. Supporting the duct segment 4 with support mechanism 20 aids in ensuring that duct segment 4 is sufficiently aligned with adjacent duct portions 6, and isolation fittings 2 to allow the material being transported to assume a steady, approximately horizontal flow. In another exemplary embodiment of the invention, support mechanism 20 comprises a weighing mechanism (e.g., scale, load cell) to weigh the duct segment 4. In yet another exemplary embodiment of the invention, the height of support mechanism 20 is adjustable to provide proper alignment of duct segment 4, isolation fittings 2, and adjacent duct portions 6.

To determine the density of the material, material free fluid, such as air, is transported through duct segment 4. As shown in step 10 of FIG. 2, duct segment 4 is weighed while the material free fluid is flowing through duct segment 4. This weight is recorded. Next, the material is introduced into the fluid, and the duct segment 4 is weighed while a mixture of fluid and material is being conveyed (step 12). To ensure an accurate measurement, the pressure in duct segment 4 of the flowing fluid is the same during the performance of both steps 10 and 12. A fluid under pressure has a greater density than the same fluid under less pressure. A difference in pressure will cause a difference in the measured weight, thus affecting the accuracy of the subsequent calculations.

The difference between these two weights (i.e., the weight of the duct segment 4 with material free fluid flow and the weight of the duct segment 4 with a mixture of material and fluid flow) is obtained by subtracting the weight of the material free fluid from the weight of the mixture (step 14). The difference corresponds to the weight of the material in the duct segment 4. This resultant weight is proportional to the mass of the material. The value of the obtained difference is then divided by the length of duct segment 4 to obtain the linear density of the material in the mixture (step 16).

Linear density is a measure of mass per distance (e.g., grams/meter, slugs/foot). In another embodiment of the invention, the linear density of the material is multiplied by the average velocity of the mixture to obtain a flow rate of the material (step 18). The average velocity may be obtained by any means well known in the art (e.g., using flow meters). Linear density, velocity, and flow rate are related by the following equation.

$$FR = \rho_L \times v, \quad (1)$$

where FR is flow rate, $\rho_L$ is linear density, and v is velocity. The units of linear density are mass/distance and the units for velocity are distance/time. Thus, the units for flow rate are mass/time (e.g., grams/sec, slugs/sec). As is well understood in the art, the units of mass are often interchanged with equivalent units of weight. Thus, flow rate may also be expressed in units of pounds/sec, for example. In step 22, the flow rate is used to determine the amount of material that has been conveyed by the pneumatic conveying system. This is determined by multiplying the flow rate by the dispense time (i.e., the amount of time at which the material has been dispensed at the determined flow rate). Flow rates may range from approximately five pounds per minute to approximately fifty pounds per minute.

Due to sensitivity limits of the of the weighing mechanism, if the combined mass of the material free air flowing through the duct segment 4 and the weight of duct segment 4, are much greater than the mass of the material in the mixture, error may be introduced into the determined weight of the material. At startup, as the pneumatic conveying system is pressurized, the mass of material free air flowing through duct segment 4 increases. If the mass of the material being transported through duct segment 4 is very small relative to the mass of material free air flowing through the duct segment 4, it may be difficult for the weighing mechanism to detect the small difference. Also, the weight of the duct segment 4 is included in the weight measurement made by the weighing device. Thus, it as is preferred that the ratio of the mass of the material free air flowing through duct segment 4 and the weight of duct segment 4, to the mass of the material flowing through the duct segment 4 be within the measuring resolution of the weighing device. High-resolution load cells are known in the art, and are suitable weighing devices. For example, a resolution as fine as 0.001% of the load cell maximum capacity and a positional resolution of less than five microns are attainable.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A method for determining, in situ, a weight of material entrained in a fluid flowing in a duct segment, said method comprising the steps of:

weighing said duct segment having material free fluid flowing therein to obtain a first weight, wherein said duct segment is in fluid communication with a conveying system;

weighing said duct segment having a mixture of material and fluid flowing therein to obtain a second weight;

subtracting said first weight from said second weight to determine, in situ, said weight of said material in said duct segment.

2. A method in accordance with claim 1, wherein said fluid comprises a gas, a liquid, or both.

3. A method in accordance with claim 1, wherein said conveying system is one of a pneumatic conveying system or a hydraulic conveying system.

4. A method in accordance with claim 1, wherein said material is selected from the group comprising granulated rock wool, granulated mineral fiber wool, glass fiber materials, cellulose fibers, expanded mica, and asbestos.

5. A method in accordance with claim 1, further comprising the step of dividing said weight of said material by a length of said duct segment to determine, in situ, a linear density of said material.

6. A method in accordance with claim 5 further comprising the step of multiplying said linear density by an average velocity of said mixture to determine, in situ, a flow rate of said material in said duct segment.

7. A method in accordance with claim 1, wherein:

said duct segment and said adjacent portions of said conveying system are approximately horizontally aligned; and said material free fluid and said mixture flows through said duct segment approximately horizontally.

8. A method in accordance with claim 1, wherein a pressure in said duct segment when said material free fluid is flowing therein is approximately equal to a pressure in said duct segment when said mixture of material and fluid is flowing therein.

9. A device for determining, in situ, a weight of a material entrained in a fluid flowing in a duct in a conveying system, said device comprising:

a duct segment in fluid communication with said conveying system; and isolation fittings for coupling said duct segment to adjacent portions of said conveying system, wherein a weight of said duct segment is measured independent of a weight of said adjacent portions of said conveying system.

10. A device in accordance with claim 9, wherein said fluid comprises a gas, a liquid, or both.

11. A device in accordance with claim 9, wherein said conveying system is a pneumatic conveying system or a hydraulic conveying system.

12. A device in accordance with claim 9, wherein said material is selected from the group comprising granulated rock wool, granulated mineral fiber wool, glass fiber materials, cellulose fibers, expanded mica, and asbestos.

13. A device in accordance with claim 9, wherein said duct segment and said adjacent portions of said conveying system are aligned to suppress flow turbulence.

14. A device in accordance with claim 9, wherein said isolation fittings, said duct segment, and said adjacent portions of said conveying system are approximately horizontally aligned.

15. A device in accordance with claim 9, wherein said isolation fittings provide approximately horizontal flow of said mixture through said duct segment.

16. A device in accordance with claim 9 further comprising a support mechanism for supporting and weighing said duct segment.

17. A device in accordance with claim 9, wherein said support mechanism aligns said duct segment, said isolation fittings, and said adjacent portions of said conveying system.

18. A device in accordance with 9, wherein said support mechanism comprising at least one of a scale and a load cell.

* * * * *